United States Patent [19]

Bock et al.

[11] Patent Number: 4,554,272
[45] Date of Patent: Nov. 19, 1985

[54] SUBSTITUTED QUINAZOLINO-1,4-BENZODIAZEPIN-6,9-DIONES AND THEIR PREPARATION

[75] Inventors: Mark G. Bock; Roger M. Freidinger, both of Hatfield,, Pa.

[73] Assignee: Merck & Co., Inc., Rahway, N.J.

[21] Appl. No.: 695,119

[22] Filed: Jan. 25, 1985

[51] Int. Cl.$^4$ ..................... A61K 31/55; C07D 403/14
[52] U.S. Cl. ............................. 514/219; 260/239.3 P; 260/239.3 D
[58] Field of Search ................. 260/239.3 P; 424/251; 514/219

[56] References Cited

U.S. PATENT DOCUMENTS 3,651,046  3/1972  Dieriea et al. .................. 260/239.3P
4,187,306  2/1980  Mayer et al. .................. 260/239.3 P Primary Examiner—Robert T. Bond
Attorney, Agent, or Firm—Daniel T. Szura; Gabriel Lopez; Hesna J. Pfeiffer

[57] ABSTRACT

Tetracyclic compounds of the formula:

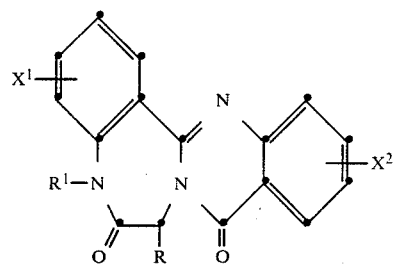

and a process for their preparation are disclosed. The compounds have cholecystokinin inhibiting activity.

11 Claims, No Drawings

SUBSTITUTED QUINAZOLINO-1,4-BENZODIAZEPIN-6,9-DIONES AND THEIR PREPARATION

BACKGROUND OF THE INVENTION

The present invention is directed to quinazolino-1,4-benzodiazepin-6,9-diones, which antagonize the function of cholecystokinins (CCK), to the preparation of these compounds, and to their pharmaceutical use.

Cholecystokinins (CCK) are neuropeptides (see, Mutt and Jorpes, *Biochem. J.*, 125, 678 (1971)) which exist in both gastrointestinal tissue and the central nervous system (V. Mutt, *Gastrointestinal Hormones*, G. B. J. Glass, ed. Raven Press, N.Y., 1980, p. 169), and include, e.g., CCK-33, a neuropeptide of thirty-three amino acids and its carboxyl terminal octapeptide, CCK-8. These molecules are believed to be physiological satiety hormones and, therefore, may play an important role in appetite regulation (G. P. Smith, Eating and Its Disorders, A. J. Stunkard and E. Stellar, Eds., Raven Press, New York, 1984, p. 67).

In addition, CCK's stimulate colonic motility, gall bladder contraction, and pancreatic enzyme secretion, and inhibit gastric emptying. CCK's reportedly also co-exist with dopamine in certain mid-brain neurons, and thus may additionally play a role in the functioning of dopaminergic systems in the brain, as well as serve as neurotramsitters in their own right. See: A. J. Prange et al., "Peptides in the Central Nervous System", *Ann. Repts. Med. Chem.*, 17, 31, 33 (1982), and references cited therein; J. A. Williams, *Biomed. Res.*, 3, 107 (1982); and J. E. Morley, *Life Sci.*, 30, 479 (1982).

Antagonists to CCK have been useful for preventing or treating CCK-related disorders of the gastrointestinal, central nervous and appetite-regulatory systems of mammals, especially of humans. Three distinct chemical classes of CCK-receptor antagonists have been reported. The first class comprises derivatives of cyclic nucleotides, of which dibutyryl cyclic GMP has been shown to be the most potent by detailed structure-function studies (see, N. Barlos et al., *Am. J. Physiol.*, 17, 268 (1980), and P. Robberecht, et al., *Mol. Pharmacol.*, 17, 268 (1980)). The second class comprises peptide antagonists which are C-terminal fragments and analogs of CCK, of which both shorter (Boc-Met-Asp-Phe-NH$_2$, Met-Asp-Phe-NH$_2$ and longer (Cbz-Tyr(SO$_3$H)-Met-Gly-Trp-Met-Asp-NH$_2$) C-terminal fragments of CCK can function as CCK-antagonists, according to recent structure-function studies (see, R. T. Jensen et al., *Biochem. Biophys. Acta.*, 757, 250 (1983), and M. Spanarkel et al., *J. Biol. Chem.*, 258, 6746 (1983)). Then, the third class of CCK receptor antagonists comprises the amino acid derivatives: proglumide, a derivative of glutaramic acid, and the N-acyl tryptophans, including para-chlorobenzoyl-L-tryptophan (benzotript), (see, W. F. Hahne et al., *Proc. Natl. Acad. Sci. U.S.A.*, 78, 6304 (1981) and R. T. Jensen et al., *Biochim. Biophys. Acta.*, 761, 269 (1983)). All of these compounds, however, are relatively weak antagonists of CCK (IC$_{50}$: generally $10^{-4}$M, but down to $10^{-6}$M in the case of the peptides) and the peptide CCK-antagonists have substantial stability and absorption problems.

The compound, 7β-[(1H-indol-3-yl)methyl]-quinazoline(3,2-D)(1,4)benzodiazepin-6,9(5H,7H)-dione of the formula (Ia):

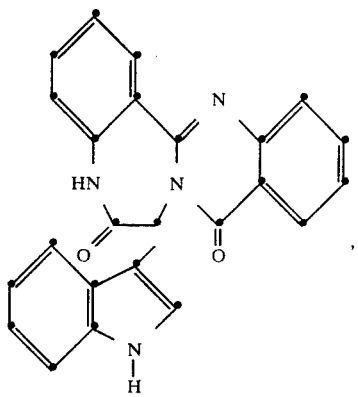

prepared by a controlled aerobic fermentation, is a CCK antagonist; it is disclosed in published European Patent Application No. 0,116,150.

A novel non-fermentation route to the compounds of formula IA and novel quinazolino-1,4-benzodiazepin-6,9-diones have been discovered having improved CCK-antagonist potency or selectivity.

SUMMARY OF THE INVENTION

Certain quinazolino-1,4-benzodiazepin-6,9-diones, their preparation and pharmaceutical use.

DETAILED DESCRIPTION OF THE INVENTION

The quinazolino-1,4-benzodiazepin-6,9-diones of this invention are embodied in compounds of the formula (I):

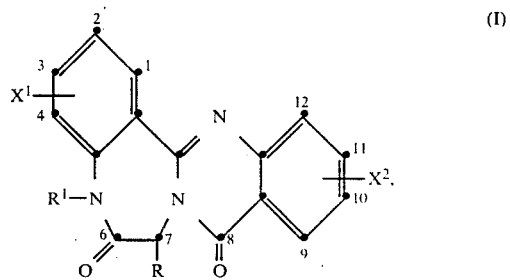

wherein:

X$^1$ and X$^2$ are independently selected from H, Br, Cl, F, OH, O-C$_1$-C$_4$-alkyl, and

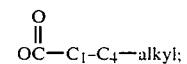

R is H; C$_1$-C$_5$-straight or branched-chain alkyl; hydroxy-C$_1$-C$_4$alkyl; C$_3$-C$_7$-cycloalkyl; C$_1$-C$_5$-aralkyl, wherein the aryl moiety is, for example, phenyl or naphthyl, which is unsubstituted or monosubstituted on the aromatic ring by Br, Cl, F, OH, O-C$_1$-C$_4$-alkyl, O-CH$_2$-phenyl,

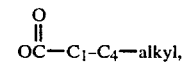

$NO_2$, CN, $CF_3$, or $OSO_3H$; $CH_2$-imidazole; $CH_2$-thiophene; $CH_2$-2-indole; $CH_2$-3-indole; $CH_2$-2-indoline; $CH_2$-3-indoline;

$CH_2CH_2SCH_3$; or

where $R^2$ is $C_1$–$C_4$-alkyl; $C_3$–$C_7$-cycloalkyl; $C_1$–$C_4$-aralkyl, wherein the aryl moiety is, for example, phenyl or naphthyl, which is unsubstituted or monosubstituted on the aromatic ring by Br, Cl, F, OH, O-$C_1$–$C_4$-alkyl,

$CH_2CH_2SCH_3$; or

$C_1$–$C_4$-alkyl, $CF_3$, $NO_2$, $NH_2$, $N(CH_3)_2$, CN or S-$C_1$–$C_4$-alkyl; 2-indole or 3-indole, which is unsubstituted or monosubstituted by F, Cl, Br, OH, $NO_2$ or O-$C_1$–$C_4$-alkyl; thiophene; imidazole; benzofuran; benzothiophene; or benzimidazole; and $R^1$ is H, $C_1$–$C_4$-alkyl or $(CH_2)_nCO_2H$, where n is 1 to 3; (excluding compounds where $X^1$ and $X^2$ are H; R is

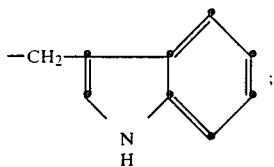

and $R^1$ is H) and pharmaceutically-acceptable salts thereof.

The term alkyl as used herein includes branched and linear moieties unless otherwise indicated.

Preferred compounds of formula I include those in which $X^1$ and $X^2$ are H; R is H, methyl, p-hydroxyphenylmethyl, or 3-indolylmethyl; $R^1$ is H, methyl or $CH_2COOH$; and the configuration at the 7-position is either R or S. These preferred compounds include 7β-[(4-hydroxyphenyl)methyl]quinazolino(3,2-D)(1,4)benzodiazepin-6,9(5H,7H)-dione, quinazoline(3,2-D)(1,4)benzodiazepin-6,9(5H,7H)-dione, 7β-methyl-quinazolino(3,2-D)(1,4)benzodiazepin-6,9(5H,7H)-dione, and 5-methyl-7β-[(1H-indol-3-yl)methyl]-quinazolino(3,2-D)(1,4)-benzodiazepin-6,9(5H,7H)-dione.

The particularly preferred compound according to the instant invention is that compound having formula I wherein the chiral configuration at the 7-position is S, $X^1$ and $X^2$ are H, R is methyl and $R^1$ is 3-indolylmethyl, named 5-methyl-7β-[(1H-indol-3-yl)methyl]-quinazolino(3,2-D)-(1,4)benzodiazepin-6,9(5H,7H)-dione.

The pharmaceutically-acceptable salts of the compounds of the instant invention include the conventional soluble, non-toxic salts of the compounds of this invention which are formed, for example, from non-toxic inorganic acids or bases or from organic acids and amines. Such conventional non-toxic salts include those derived from inorganic acids, such as hydrochloric, hydrobromic, sulfuric, sulfamic, phosphoric or nitric; from very strong organic acids, such as ethane disulfonic, trifluoroacetic or isethionic acids and the like; or, if R is $CH_2$-monosubstituted phenyl where the substituent is $OSO_3H$, from inorganic bases, such as lithium hydroxide, sodium hydroxide, potassium hydroxide, calcium hydroxide, magnesium hydroxide, and the like, or from organic amines, such as trimethyl, triethyl, diisopropylethyl amines and the like.

Compounds according to formula I of the instant invention and salts thereof may be produced by one or more of three schemes set out below:

SCHEME 1

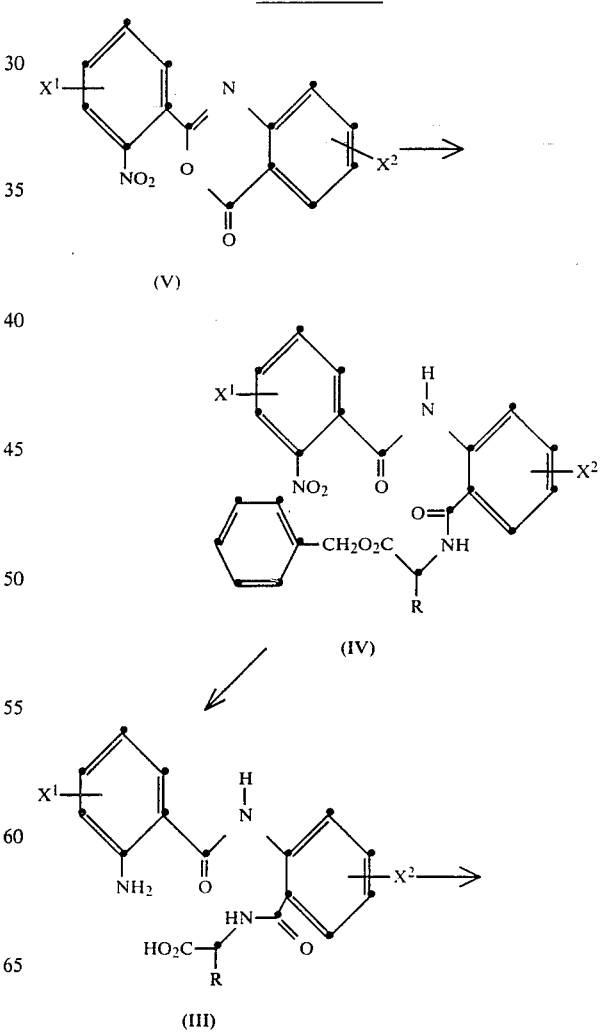

-continued
SCHEME 1

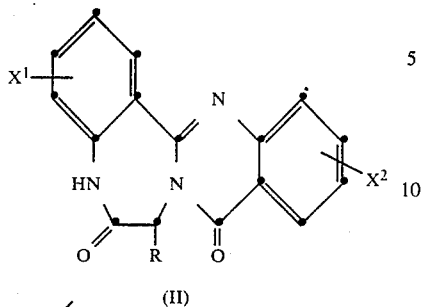

(II)

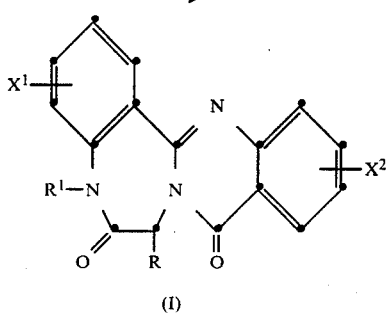

(I)

According to Scheme 1, compounds of the general formula V may be obtained according to the procedure described in *J. Liebigs Annalen,* (1909) 367, 121, or by other convenient adaptations, one of which is to react an anthranilic acid derivative with 2-nitrobenzoylchloride in tetrahydrofuran at room temperature in the presence of triethylamine. These 3,1-benzoxazin-4-ones V are then treated with an amino acid ester hydrochloride, such as tryptophan benzyl ester hydrochloride, O-benzyl-tyrosine benzyl ester hydrochloride, or alanine benzylester hydrochloride, in a dry aprotic solvent, such as acetonitrile, tetrahydrofuran, xylene, toluene, N,N-dimethylformamide, dimethylsulfoxide, and the like, at from 0° C. to the boiling point of the solvent, for 0.5 to 36 hours, to produce compounds of formula IV. Preferably the reaction is carried out in dimethylformamide at 80° C. for five hours.

Compounds of general formula III are then produced by reducing compounds of general formula IV using a suitable hydrogen/catalyst system. Examples of suitable catalysts include palladium-on-carbon, platinum-on-carbon, platinum oxide, and the like. Preferably the reaction is carried out in a solvent like ethanol or ethyl acetate, under 50 to 55 psi hydrogen pressure for 5 hours in a Parr apparatus using a palladium-on-carbon catalyst.

The resulting amino acids (III) are then cyclodehydrated to give the tetracyclic compounds of general formula II. This transformation may be carried out by heating compounds of general formula III, with or without a solvent, at from 50° to 350° C., for from 0.1 to 5 hours. Preferably the reaction is carried out by heating a finely ground sample of a compound of formula III at 250° C. for 0.5 hours.

Compounds of general formula I may then be obtained by treating compounds of general formula II with a base in a suitable solvent followed by the addition of an appropriate electrophilic alkylating agent. Examples of suitable bases include sodium hydride, potassium hydride, lithium diisopropylethylamide, and the like; suitable solvents include tetrahydrofuran, N,N-dimethylformamide, dioxane, and the like; and appropriate alkylating agents include iodomethane, iodoethane, n-propyl-p-toluenesulfonate, ethyl bromoacetate and the like.

SCHEME 2

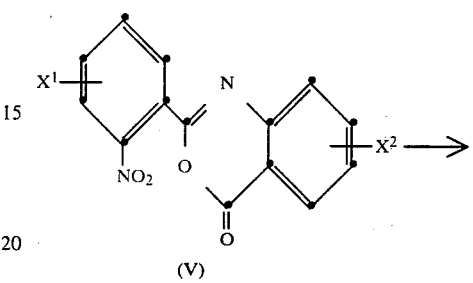

(V)

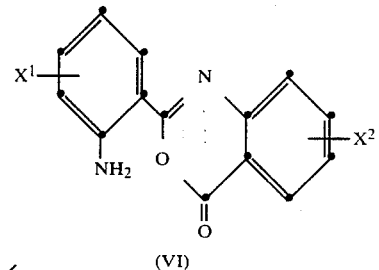

(VI)

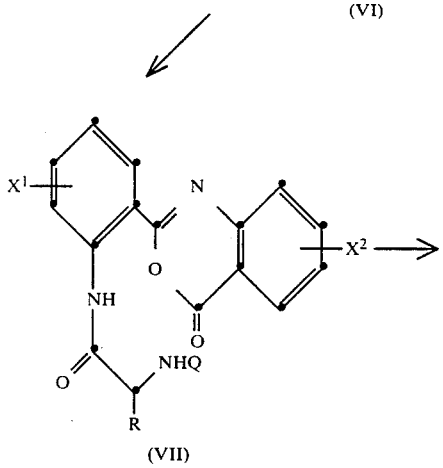

(VII)

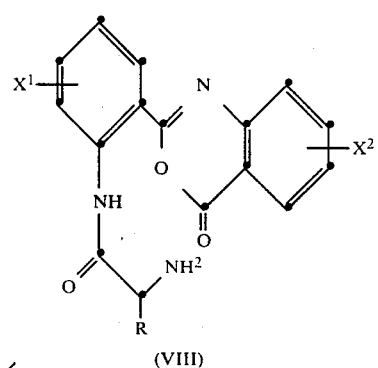

(VIII)

-continued
SCHEME 2

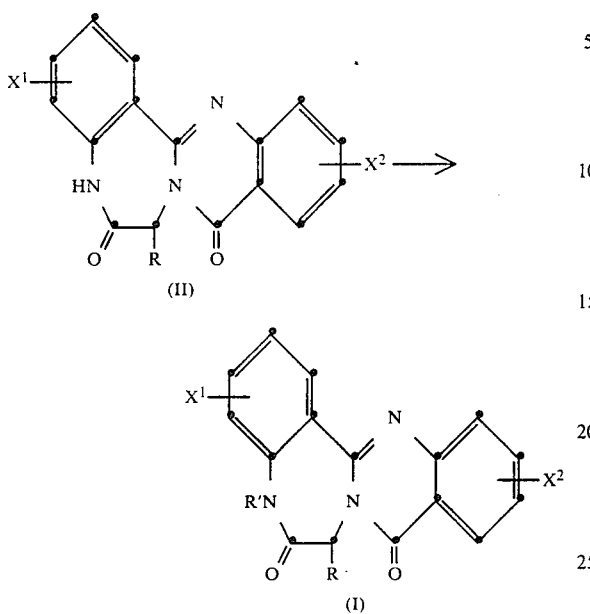

According to Scheme 2, compounds of general formula V may be reduced selectively to give amino-3,1-benzoxazin-4-ones of general formula VI. This transformation is effected by treating compounds of formula V in a solvent, like ethanol or ethyl acetate, with a suitable catalyst, such as palladium-on-carbon, and stirring the resulting suspension for from 0.1 to 10 hours under an atmosphere of hydrogen at 1 atm. of pressure.

The resulting amino compounds (IV) may then be acylated with a suitably-protected amino acid in an inert solvent at temperatures of from −30° C. to the boiling point of the solvent, preferably at room temperature, in the presence of suitable coupling reagent, such as dicyclohexylcarbodiimide, 1-ethyl-3-(3-dimethylaminopropyl)carbodiimide hydrochloride, carbonyldiimidazole, or the like. Examples of suitably-protected amino acids include Nα-tert-butyloxycarbonyl alanine, Nα-tert-butyloxycarbonyl glycine, Nα-tert-butyloxycarbonyltryptophan, and the like. Preferred solvents for this process are methylene chloride or N,N-dimethylformamide.

Next, the amino protecting group Q in the compounds having the formula VII may be cleaved under appropriate conditions to give compounds of general formula VIII. For example, compounds of general formula VII may be dissolved in a solvent like methylene chloride or ethyl acetate and the resulting solution may be treated with a continuous stream of hydrogen chloride or hydrogen bromide gas at 0° C. until cleavage of the protecting group Q, has been completed. Alternatively, compounds of general formula VIII may be prepared directly by mixing compounds of general formula VI in a solvent, such as methylene chloride, dioxane, or tetrahydrofuran, with amino acid halides, such as tryptophan acid chloride hydrochloride, or glycine acid chloride hydrochloride, at room temperature for 0.1 to 10 hours.

Cyclization of compounds of general formula VIII to give compounds of general formula II is then carried out according to the cyclization procedure described for the preparation of compounds of general formula II in Scheme 1. Preferably in this instance, compounds of general formula VIII are dissolved in N,N-dimethylformamide and heated at 80° for 5 hours. Final conversion of compounds having formula II to compounds of general formula I is accomplished using methology described for this process in Scheme 1.

SCHEME 3

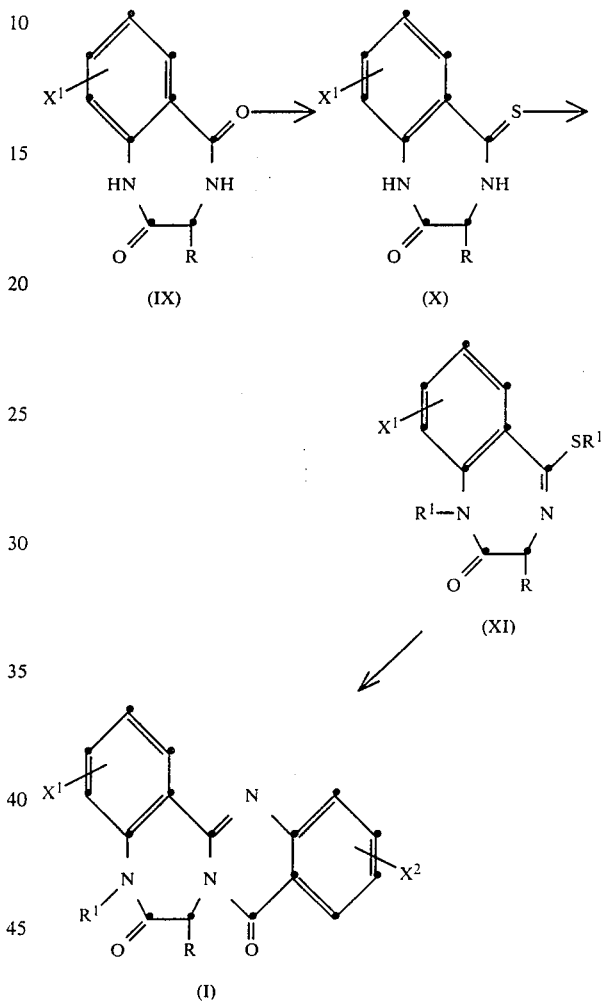

According to Scheme 3, compounds of general formula IX, obtained according to the method described in J. Org. Chem., (1980) 45, 1675, are first transformed to the thioamides of the general formula X by the action of phosphorus pentasulfide in benzene, toluene, or xylene on formula IX compounds. Preferably, 2,4-bis-(4-methoxyphenyl)-2,4-dithioxo-1,3,2,4-dithiadiphosphetane is mixed in toluene with formula IX compounds and heated for 1.5 hours or until conversion is complete.

Compounds of general formula X, thus obtained, are then converted to compounds of general formula XI using an alkyl halide or alkyl sulfonate with a suitable base in an appropriate solvent, at from −10° C. to the boiling point of the solvent. Examples of suitable alkyl halides and alkyl sulfonates include iodoethane, 2-iodopropane, n-butyl-p-toluene sulfonate, and the like, while suitable bases include sodium hydride, potassium hydride, sodium methoxide, and the like. N,N-dimethylformamide, tetrahydrofuran, ethanol, methanol, and the like are appropriate solvents. Preferably, the reaction is carried out under phase transfer conditions whereby compounds of general formula X are suspended in a two phase system of water-toluene containing sodium hydroxide and tetrabutylammonium hydrogen sulfate and are subsequently treated with iodomethane at from 0° C. to 27° C. for 0.2 to 3 hours.

The resulting compounds of general formula XI are subsequently mixed intimately with an anthranilic acid derivative and heated either with a solvent, such as xylene or N,N-dimethylformamide, or without a solvent, at from 50° C. to 350° C., for 0.2 hours to 10 hours. Preferably, the reaction is carried out by combining compounds of general formula XI with anthranilic acid and heating the mixture at 175° C. for 3 hours to give compounds of general formula I.

Pharmaceutically-acceptable salts of the compounds according to the instant invention which have the general formula I may then be synthesized by conventional chemical means by suspending compounds of formula I in a solvent, such as water, methanol, ethanol, ethyl acetate, tetrahydrofuran, or other suitable organic solvent or combinations of solvents, and treating the resulting reaction mixture with stoichiometric amounts of, or with an excess of, the desired salt-forming inorganic or organic acid or base. Examples of appropriate salt-forming acids include hydrochloric, hydrobromic, sulfuric, sulfamic, phosphoric, nitric, ethane disulfonic, trifluoroacetic or isethionic acids and the like, while examples of salt-forming bases include lithium hydroxide, sodium hydroxide, potassium hydroxide, calcium hydroxide, magnesium hydroxide, trimethylamine, triethylamine, diisopropylethylamine or N-methylpiperidine and the like.

Chiral acylating and alkylating agents of both configurations may be used for the production of analogs of compounds according to the instant invention with the configuration of the asymmetric center at position 7 being determined by the choice of starting materials.

Screening of the novel compounds according to the present invention to determine biological activity and obtain an $IC_{50}$ value for them (in order to identify significant CCK-antagonism) is accomplished using an $^{125}I$-CCK receptor binding assay and in vitro isolated tissue preparations. These tests involve the following:

CCK Receptor Binding (pancreas) Method

CCK-33 is radiolabeled with $^{125}I$-Bolton Hunter reagent (2000 Ci/mmole), as described by Sankara et al. (*J. Biol. Chem.*, 254, 9349-9351, 1979). Receptor binding is performed according to Innis and Snyder (*Proc. Natl. Acad. Sci.*, 77, 6917-6921, 1980), with the minor modification of adding the additional protease inhibitors, phenylmethane sulfonyl fluoride and o-phenanthroline, which have no effect on the $^{125}I$-CCK receptor binding assay.

The whole pancreas of a male Sprague-Dawley rat (200-350 g), which has been sacrificed by decapitation, is dissected free of fat tissue and homogenized in 20 volumes of ice-cold 50 mM Tris HCl (pH 7.7 at 25° C.) with a Brinkman Polytron PT-10. The homogenates are centrifuged at 48,000 g for 10 minutes, then the resulting pellets are resuspended in Tris Buffer, centrifuged as above, and resuspended in 200 volumes of binding assay buffer (50 mM Tris HCl, pH 7.7 at 25° C., 5 mM dithiothreitol, 0.1 mM bacitracin, 1.2 mM phenylmethane sulfonyl fluoride and 0.5 mM o-phenanthroline).

For the binding assay, 25 $\mu$l of buffer (for total binding), or unlabeled CCK-8 sulfate sufficient to give a final concentration of 1 $\mu$M of CCK-8 (for nonspecific binding), or the compounds of the formula of the compounds according to the instant invention (for determination of antagonism to $^{125}I$-CCK binding) and 25 $\mu$l of $^{125}I$-CCK-33 (30,000-40,000 cpm), are added to 450 $\mu$l of the membrane suspensions in microfuge tubes. All assays are run in duplicate or triplicate, and the reaction mixtures are incubated at 37° C. for 30 minutes and centrifuged in a Beckman Microfuge (4 minutes) immediately after adding 1 ml of ice-cold incubation buffer. The supernatant is aspirated and discarded, and the pellets are counted with a Beckman Gamma 5000. For Scatchard analysis to determine the mechanism of inhibition of $^{125}I$-CCK binding by the most potent compounds (*Ann. N.Y. Acad. Sci.*, 51, 660, 1949), $^{125}I$-CCK-33 is progressively diluted with increasing concentrations of CCK-33.

CCK Receptor Binding (brain) Method

CCK-33 is radiolabeled and the binding is performed according to the description for the pancreas method, with modifications according to Saito et al., *J. Neurochem.*, 37, 483-490, 1981.

Male Hartley guinea pigs (300-500 g) are sacrificed by decapitation, and the brains are removed and placed in ice-cold 50 mM Tris HCl (Trizma-7.4) [pH 7.4 at 25° C.]. The cerebral cortex is dissected and used as a receptor source and each gram of fresh guinea pig brain tissue is homogenized in 10 ml of Tris/Trizma buffer with a Brinkman polytron PT-10. The homogenates are centrifuged at 42,000 g for 15 minutes, then the resulting pellets are resuspended in 80 volumes of binding assay buffer (10 mM N-2-hydroxyethyl-piperazine-N'-2-ethanesulfonic acid (HEPES), 5 mM $MgCl_2$, 1 mM ethylene glycol-bis($\beta$-amino-ethyl-ether-N,N'-tetraacetic acid (EGTA), 0.4% BSA and 0.25 mg/ml bacitracin, pH 6.5).

The remainder of the inding assay method is as described for the pancreas method, except that the reaction mixtures are incubated at 25° C. for 2 hours before concentration.

An additional method of confirming competitive antagonism of CCK which may be used is the following:

Isolated Guinea Pig Gall Bladder Method

The two halves of the gall bladders, free of adjacent tissue, of male Hartley guinea pigs (400-600 g), which have been sacrificed by decapitation, are suspended under 1 g tension along the axis of the bile duct in 5 ml organ bath, containing a Kreb's bicarbonate solution of 118 mM NaCl, 4.75 mM KCl, 2.54 $CaCl_2$, 1.19 mM $KH_2PO_4$, 1.2 mM $MgSO_4$, 25 mM $NaHCO_3$ and 11 mM dextrose, which is maintained at 32° C. and bubbled with a mixture of 95% $O_2$ and 5% $CO_2$. The tissues are washed every 10 minutes for 1 hour to obtain equilibrium prior to the beginning of the study and the isometric contractions of the strips are recorded using Statham (60 g: 0.12 mm) strain gauges and a Hewlett-Packard 77588 recorder.

CCK-8 is added cumulatively to the baths and $EC_{50}$'s are determined using regression analysis. After washout (every 10 minutes for 1 hour), the compound to be tested is added at least 5 minutes before the addition of CCK-8 and the $EC_{50}$ of CCK-8 in the presence of compound to be tested is similarly determined.

A shift to the right of the CCK dose response curve without reduction of the maximal contractile response, indicates competitive antagonism of CCK from this method.

The ability of the compounds of the instant invention to antagonize CCK makes these compounds useful as pharmaceutical agents for mammals, especially for humans, for the treatment and prevention of disorders wherein CCK may be involved. Examples of such disease states include gastrointestinal disorders, especially such as irritable bowel syndrome or ulcers, excess pancreatic or gastric secretion, acute pancreatis, or motility disorders; central nervous system disorders, caused by CCK interactions with dopamine, such as neuroleptic disorders, tardive dyskinesia, Parkinson's disease, psychosis or Gilles de la Tourette Syndrome; and disorders of appetite regulatory systems.

The present compounds may also be useful to study the CCK pathway in animal systems.

The compounds of the instant invention or pharmaceutically-acceptable salts thereof, may be administered to a human subject either alone or, preferably, in combination with pharmaceutically-acceptable carriers or diluents, in a pharmaceutical composition, according to standard pharmaceutical practice. The compounds can be administered orally or parenterally, including intravenous, intramuscular, intraperitoneal, subcutaneous and topical administration.

For oral use of a formula I antagonist of CCK, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a formula I compound, or a salt thereof, is used or administered to a human subject, the daily dosage will normally be determined by the prescribing physician. Moreover, the dosage will vary according to the age, weight, and response of the individual patient, as well as the severity and nature of the patient's symptoms. In most instances, an effective daily dosage will be in the range of from about 1 mg to about 1500 mg, and preferably, of from 10 mg to about 500 mg administered in single or divided doses. In some cases, however, it may be necessary to to use dosages outside these limits.

The invention is further defined by references to the following examples which are intended to be illustrative and not limiting.

EXAMPLE 1

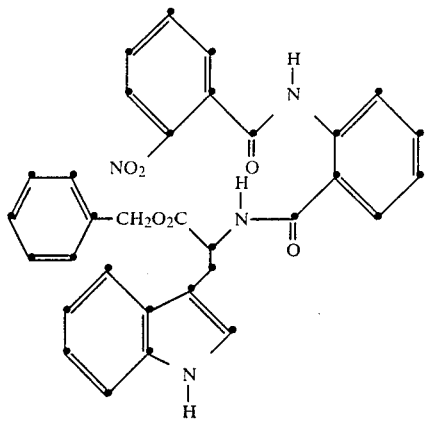

Synthesis of benzyl 2(D)-[2'-(2-nitrobenzoyl)aminobenzoyl]-amino-3-(1H-indol-3-yl)propanoate To 2.40 g (8.94 mmole) of nitrobenzoxazin-4-one in 3 ml of dry dimethylformamide was added 3.25 (9.82 mmole) of L-tryptophan benzylester hydrochloride and the resulting mixture was heated at 105° C. for 40 hours. The solvent was removed under reduced pressure to give an oil, which was partitioned between ethyl acetate and 10% citric acid solution. The organic phase was separated, washed with water and brine, then dried and concentrated. Flash chromatography on silica gel (hexane-ethyl acetate 1:1 v/v) gave the product as a chromatographically-homogeneous yellow foam (3.39 g).

PMR (CDCl$_3$): according to theory.

Elemental Analysis: $C_{32}H_{24}N_4O_6 \cdot \frac{1}{2}H_2O$: Calc'd For: N, 9.83; C, 67.48; H, 4.42. Found: N, 9.77; C, 67.26; H, 4.59.

EXAMPLE 2

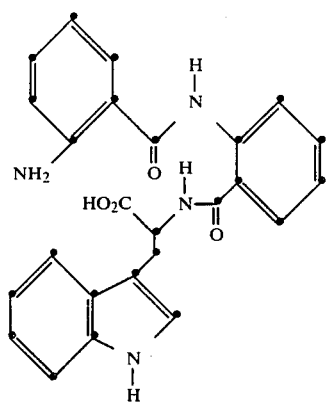

Synthesis of 2(D)-[2'-(2-aminobenzoyl)aminobenzyl]amino-3-(1H-indol-3-yl)propanoic acid To a solution of 50 ml of absolute ethanol was added 750 mg (1.33 mmole) of the nitrobenzyl ester and 133 mg of palladium (10% on carbon) catalyst and the resulting suspension was hydrogenated on a Parr apparatus for 12 hours at 50 psi. The reaction mixture was filtered through a pad of Celite and the filtrate was concentrated to give the crude product. Flash chromatography on silica gel (chloroform-methanol-acetic acid 90:10:1) afforded a 92% yield of the analytical product as an off-white solid.

IR(KBr, partial): 3350, 1680, 1570, 1440, 1400, 745 cm$^{-1}$.

MS(FAB): 465 (M+Na), 487 (M+2Na-H).

PMR(DMSO-d$_6$): 3.18 (1H, dxd, J=15.6), 3.42 (1H, dxd, J=15.5), 4.23 (1H, b.d, J=5), 6.65 (3H, m), 6.72 (2H, m), 6.95 (1H, t, J=5), 7.06 (2H, m), 7.24 (2H, m), 7.49 (3H, m), 7.56 (1H, d, J=5), 8.18 (1H, b.s), 8.55 (1H, d, J=5).

EXAMPLE 3

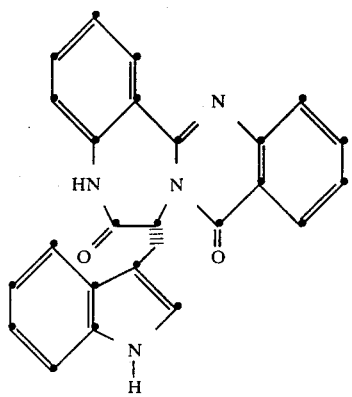

Synthesis of 7α-[1H-indol-3-yl)methyl]quinazolino(3,2-D)-1,4-benzodiazepin-6,9(5H,7H)-dione hydrate The amino acid having formula III which corresponds to the above-named compound (4 mg, 0.01 mmole) was immersed in a preheated oil bath at 250°–255° C. for 45 minutes until TLC analysis indicated all starting material had been consumed. The reaction mixture was cooled and applied directly onto a precoated thin layer silica gel plate (Merck 60F-254, 0.25 mm × 20 × 20 cm) and then eluted with chloroform-methanol (9:1 v/v). The only isolable product II (2.5 mg) proved to be identical in all respects (TLC, PMR, mass spec), except rotation of polarized light, with the product prepared and identified in United States Application, Ser. No. 509,883, which is incorporated herein, by reference.

EXAMPLE 4

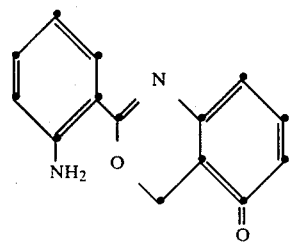

Synthesis of 2-(2-aminophenyl)-3,1-benzoxazin-4-one 2-(2-Nitrophenyl)-3,1-benzoxazin-4-one (1.1 g, 4.10 mmole) was suspended in 40 ml of ethyl acetate, with platinum oxide (100 mg) being added, and the resulting reaction mixture was hydrogenated at atmospheric pressure with vigorous stirring. After 3 hours, the catalyst was removed and the solvent was rotoevaporated. The residual yellow oil was subjected to flash chromatography to give a homogeneous product. Recrystallization from acetone provided the analytical sample, m.p. 163°–165° C. (lit.* 162° C.).

*G. Schroeter and O. Eisleb, J. Liebigs Ann., (1909) 367, 121.

PMR according to theory.

Elemental Analysis: C$_{14}$H$_{10}$N$_2$O$_2$: Calc'd For: N, 11.76; C, 70.58; H, 4.23. Found: N, 11.33; C, 70.25; H, 4.53.

EXAMPLE 5

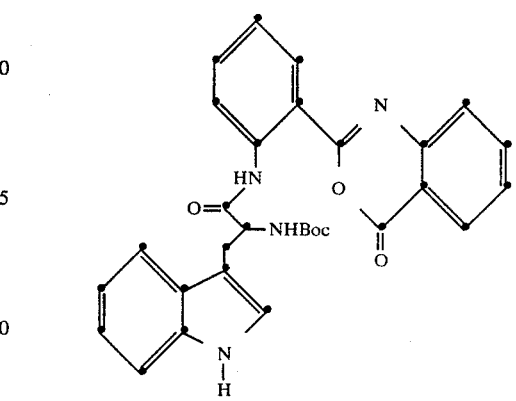

Synthesis of 2-2-[2-(D)-(tert-butyloxycarbonyl)amino-3-(1H-indol-3-yl)propanoyl]aminophenyl-3,1-benzoxazin-4-one 2-(2-Aminophenyl)-3,1-benzoxazin-4-one (490 mg, 2.05 mmole) was combined with tert-butyloxycarbonyl-D-tryptophan (630 mg, 2.05 mmole) in 5 ml of dry dimethylformamide and 280 mg (2.05 mmole) of 1-hydroxybenzotriazole and 280 μl of triethylamine was added to this reaction mixture. The solution was stirred and then treated with 2.05 ml of a 1 molar solution of dicyclohexylcarbodiimide in methylene chloride. The reaction was protected from moisture and stirred at room temperature overnight (approximately 14 hours), whereupon an additional equivalent of each of tert-butyloxycarbonyl-D-tryptophan and dicyclohexylcarbodiimide was added and stirring was continued.

After 56 hours, the reaction was filtered and the filtrate concentrated in vacuo, with the residue being partitioned between ethylacetate and saturated sodium bicarbonate solution. The phases were separated and the organic layer was washed with sodium bicarbonate solution and brine. Rotoevaporation afforded a brown oil from which the desired compound was isolated in pure form via silica gel chromatography (hexane-ethyl acetate elution, 2:1 v/v). In this way, 210 mg of product was obtained in addition to 240 mg of starting benzoxazin-4-one (the PMR spectrum was in accord with theory).

Elemental Analysis: C$_{30}$H$_{28}$N$_4$O$_5$.H$_2$O: Calc'd For: N, 10.32; C, 66.41; H, 5.57. Found: N, 10.10; C, 66.04; H, 5.59.

EXAMPLE 6

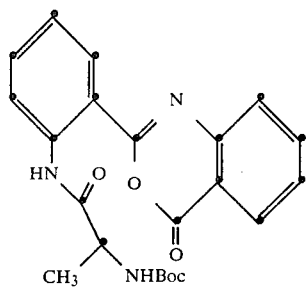

Synthesis of
2-[2(L)-(tert-butyloxycarbonyl)aminopropanoyl]amino-
phenyl-3,1-benzoxazin-4-one 2-(2-Aminophenyl)-3,1-benzoxazin-4-one (280 mg, 1.17 mmole) in 10 ml of dry methylene chloride was treated with tert-butyloxycarbonyl-L-alanine (225 mg, 1.18 mmole) and 1-ethyl-3-(3-dimethylaminopropyl)-carbodiimide hydrochloride (226 mg, 1.18 mmole). The resulting mixture was protected from moisture and the pH was adjusted to approximately 8 with triethylamine (167 μl). After 70 hours, the reaction mixture was diluted to 50 ml with methylene chloride and washed, in succession, with 10% citric acid solution, saturated sodium bicarbonate solution and brine. Rotoevaporation afforded the crude product which was subjected to chromatography on silica gel (chloroform-methanol 97:3) to give 120 mg of the analytical sample as an off-white solid, in addition to 200 mg of starting material (benzoxazin-4-one). The recovered starting material was recycled twice to give 6 in 87% over-all yield.

PMR (CDCl$_3$): in accord with structure assignment.

EXAMPLE 7

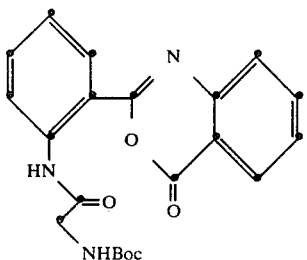

Synthesis of
2-[2-(tert-butyloxycarbonyl)aminoethanoyl]aminophe-
nyl-3,1-benzoxazin-4-one Using identical reaction conditions as described for the synthesis of the compounds of formula VII of Scheme 2 above, 480 mg (2.0 mmole) of 2-(2-aminophenyl)-3,1-benzoxazin-4-one was reacted with 525 mg (3.0 mmole) of tert-butyloxycarbonylglycine to give 170 mg of the chromatographically-homogeneous titled compound in 60% overall yield after three cycles.

The PMR spectrum confirmed its structure.

EXAMPLE 8

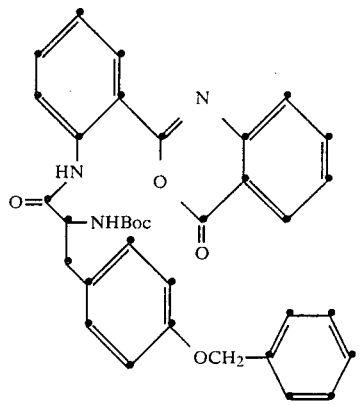

Synthesis of
2-[2(L)-(tert-butyloxycarbonyl)amino-3-(4-benzyloxy)-
phenylpropanoyl]aminophenyl-3,1-benzoxazin-4-one Using reaction conditions as described for the synthesis of compounds having formula VII of Scheme 2, 800 mg (3.4 mmole) of 2-(2-aminophenyl)-3,1-benzoxazin-4-one was reacted with 1.26 g (3.4 mmole) of 2-tert-butyloxycarbonylamino-3-(4-benzyloxyphenyl)-propanoic acid to give 1.95 g of the above-titled compound after silica gel chromatography.

IR (KBr, partial): 3350, 1765, 1680, 1500, 1240, 1220, 1010, 730 cm$^{-1}$.

PMR (CDCl$_3$): confirms structure.

EXAMPLE 9

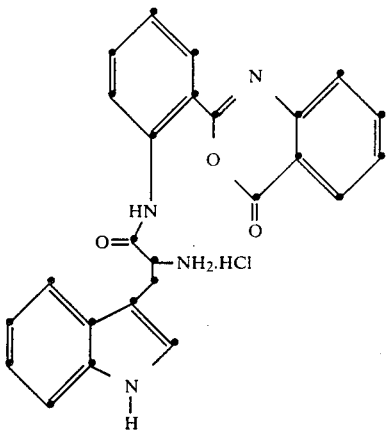

Synthesis of
2-2-[2(D)-amino-3-(1H-indol-3-yl)propanoyl]amino-
phenyl]aminophenyl-3,1-benzoxazin-4-one
hydrochloride Method A 2-2-[2(D)-(tert-butyloxycarbonyl)amino-3-(1H-indol-3-yl)-propanoyl]aminophenyl-3,1-benzoxazin-4-one (50 mg) was dissolved in 5 ml of ethyl acetate, cooled to 0° C., and treated with a stream of hydrogen chloride gas. After 30 minutes, the solvent and excess reagent were removed in vacuo, with the residual solid being re-dissolved in ethyl acetate and again concentrated under reduced pressure to remove traces of HCl gas.

PMR (CD3OD) analysis of the crude product showed no tert-butyloxycarbonyl group. The spectrum was in accord with structure assignment. The titled HCl salt was not further purified.

IR (KBr, partial): 3375, 1765, 1695, 1600, 1445, 1300, 1220, 770, 745 cm$^{-1}$.

Method B

A solution of 2-(2-aminophenyl)-3,1-benzoxazin-4-one (940 mg, 3.94 mmole) in 60 ml of tetrahydrofuran was treated with 40 ml of tetrahydrofuran containing 1.03 g (4.00 mmole) of D-tryptophan acid chloride hydrochloride. Within minutes a voluminous precipitate had formed. Stirring was continued three hours more and the reaction mixture was filtered, with the solid being washed with tetrahydrofuran and dried. The titled product was chromatographically-homogeneous, $R_f$=0.68 (80:10:1 chloroform-methanol-ammonia).

The PMR spectrum of the titled compound confirmed its structure and was identical with the spectrum of the same produce obtained via Method A.

EXAMPLE 10

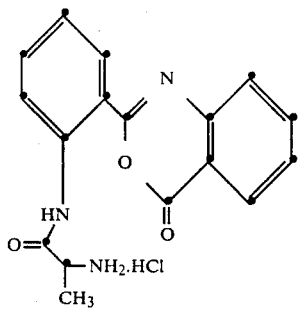

Synthesis of
2-[2(L)-aminopropanoyl]aminophenyl-3,1-benzoxazin-4-one hydrochloride 2-[2(L)-(tert-butyloxycarbonyl)aminopropanoyl]aminophenyl-3,1-benzoxazin-4-one (41 mg) was reacted in ethyl acetate with hydrogen chloride gas under identical reaction conditions as described for the synthesis of compounds of Example 9, Method A, to afford the above-titled compound.

PMR analysis confirmed the structure assignment.

EXAMPLE 11

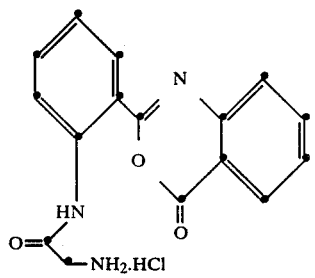

Synthesis of
2-[2-aminoethanoyl]aminophenyl-3,1-benzoxazin-4-one hydrochloride

2-[2-(tert-butyloxycarbonyl)aminoethanoyl]aminophenyl-3,1-benzoxazin-4-one (45 mg) was reacted in ethyl acetate with hydrogen chloride under reaction conditions as described for the synthesis of compounds of Example 9, Method A, to afford the above-titled compound.

PMR analysis of the product confirmed the structure assignment.

EXAMPLE 12

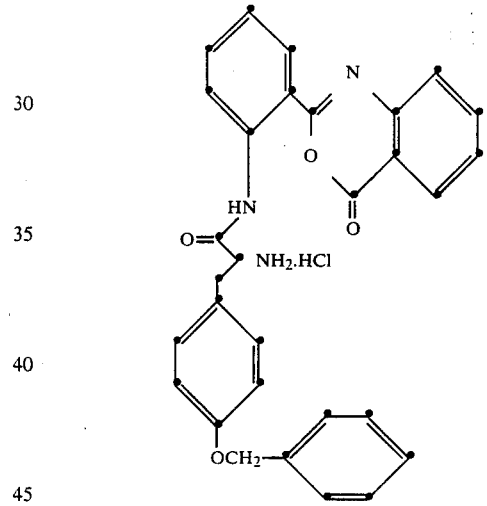

Synthesis of 2-[2(L)-amino-3-(4-benzyloxy)phenyl propanoyl]aminophenyl-3,1-benzoxazin-4-one hydrochloride 2-[2(L)-(tert-butyloxycarbonyl)amino-3-(4-benzyloxy)phenylpropanoyl]aminophenyl-3,1-benzoxazin-4-one (1.5 g, 2.54 mmole) was dissolved in 70 ml of ethyl acetate and converted to its amine hydrochloride using reaction conditions as described for the synthesis of compounds of Example 9, Method A. PMR analysis of the product confirmed the structure assignment.

IR (KBr, partial): 1765, 1700, 1605, 1510, 1240, 1220, 1010, 770 cm$^{-1}$.

EXAMPLE 13

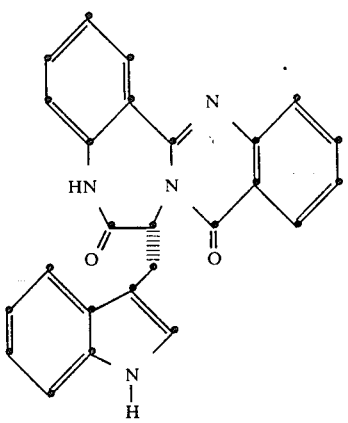

Synthesis of 7α-[(1H-indol-3-yl)methyl]quinazolino(3,2-D)-1,4-benzodiazepin-6,9(5H,7H)-dione hydrate 2-2-[2(D)-Amino-3-(1H-indol-3-yl)propanoyl]aminophenyl]aminophenyl-3,1-benzoxazin-4-one hydrochloride (240 mg, 0.52 mmole) was dissolved in 15 ml of dimethylformamide and heated at 95° C. for 6 hours. The reaction mixture was cooled and poured into 20 ml of water to precipitate the titled product. The analytical sample (180 mg) was obtained via preparative thick layer chromatography (chloroform-methanol-ammonia 80:10:1 v/v); $R_f$=0.43.

IR (KBr, partial): 3350, 1680, 1590, 770, 740 cm$^{-1}$.
MS(FAB): 406 (M+).
PMR (CD$_3$OD): 2.97 (1H, dxd, J=15.9), 3.15 (1H, dxd, J=15.9), 6.71 (1H, t, J=9, 7α proton), 6.85 (1H, s, indole C-2), 6.95 (1H, t, J=8), 7.03 (1H, t, J=8), 7.23 (1H, d, J=8), 7.28 (1H, d, J=8), 7.36 (1H, d, J=8), 7.49 (2H, m), 7.73 (2H, m), 7.82 (1H, t, J=8), 8.14 (1H, dxd, J=8.1), 8.25 (1H, dxd, J=8.1).
Elemental Analysis: C$_{25}$H$_{18}$N$_4$O$_2$.¾H$_2$O: Calc'd For: N, 13.34; C, 71.50; H, 4.68. Found: N, 13.24; C, 71.54; H, 4.36.

EXAMPLE 14

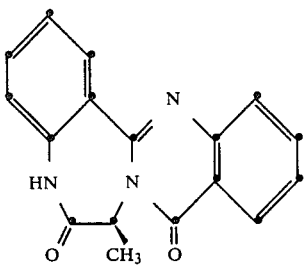

Synthesis of 7β-methylquinazolino(3,2-D)(1,4)benzodiazepin-6,9-(5H,7H)-dione 2-[2(L)-aminopropanoyl]aminophenyl-3,1-benzoxazin-4-one hydrochloride (52 mg, 0.15 mmole) was converted to the above-titled compound using reaction conditions as described for the synthesis of the compound of Example 13. The product was obtained in 90% yield. The analytical sample was recrystallized from ethylacetate, m.p. 290°-291° C.

IR (KBr, partial): 1680, 1605, 1595, 1150, 780, 770 cm$^{-1}$.

MS(20 ev): 291 (M+), 248, 247, 194.

PMR (DMSO-d$_6$): 1.20 (CH$_3$, d, J=7.6), 6.24 (H$_7$, q, J=7.6), 7.22 (H$_4$, d, J=8.3), 7.35 (H$_2$, t, J=7.4), 7.59 (H$_{11}$, t, J=7.8), 7.62 (H$_3$, t, J=8.3), 7.76 (H$_{13}$, d, J=8.3), 7.89 (H$_{12}$, t, J=8.3), 8.08 (H$_2$, d, J=8.1), 8.21 (H$_{10}$, d, J=8.1), 10.77 (NH, br, s).

Elemental Analysis: C$_{17}$H$_{13}$N$_3$O$_2$.0.3H$_2$O: Calc'd For: N, 14.16; C, 68.82; H, 4.62. Found: N, 14.35; C, 68.65; H, 4.41.

EXAMPLE 15

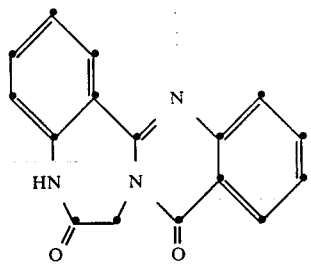

Synthesis of quinazolino(3,2-D)(1,4)benzodiazepin-6,9(5H,7H)-dione

2-[2-Aminoethanoyl]aminophenyl-3,1-benzoxazin-4-one hydrochloride (40 mg) was converted to the titled compound using reaction conditions as described for the synthesis of the compound of Example 13, with a realized yield of 93%. The analytical sample was recrystallized from ethyl acetate, m.p. 318°-319° C.

IR (KBr, partial): 1695, 1590, 1485, 770 cm.

MS (20 ev): 277 (M+), 265, 234, 146.

PMR (DMSO-d$_6$): 4.2 (H$_7$, br, s), 5.4 (H$_7$, br, s), 7.23 (H$_4$, d, J=8.3), 7.37 (H$_2$, t, J=7.5), 7.58 (H$_{11}$, t, J=7.7), 7.63 (H$_3$, t, J=8.3), 7.76 (H$_{13}$, d, J=8.2), 7.89 (H$_{12}$, t, J=8.2), 8.08 (H$_1$, d, J=8), 8.21 (H$_{10}$, d, J=8.1), 10.70 (NH, br, s).

Elemental Analysis: C$_{16}$H$_{11}$N$_3$O$_2$: Calc'd For: N, 14.16; C, 69.31; H, 3.99. Found: N, 13.90; C, 69.19; H, 3.94.

EXAMPLE 16

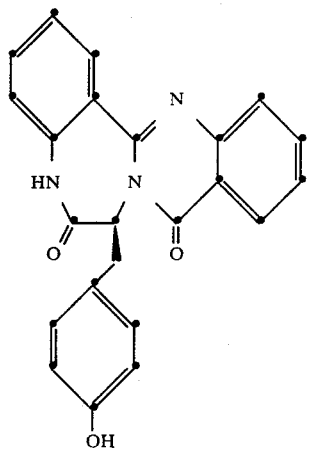

Synthesis of 7β-[(4-hydroxyphenyl)methyl]quinazolino(3,2-D)(1,4)-benzodiazepin-6,9(5H,7H)-dione hydrate 2-[2(L)-amino-3-(4-benzyloxy)phenylpropanoyl-]aminophenyl-3,1-benzoxazin-4-one hydrochloride (210 mg) was converted to 7β-[(4-benzyloxyphenylmethyl]-quinazolino(3,2-D)(1,4)benzodiazepin-6,9(5H,7H)-dione using identical reaction conditions as described for the preparation of the compound of Example 13. Proton magnetic resonance (CD₃OD) of the crude product confirmed the structure. This crude material, (200 mg) was then dissolved in 25 ml of absolute ethanol, treated with 50 mg of palladium catalyst (10% on charcoal) and hydrogenated at 45 psi for 5.5 hours. The reaction mixture was filtered through Celite and the filtrate was concentrated to give a semi-solid. Silica gel chromatography (chloroform-methanol-acetic acid 90:10:1 v/v) afforded the analytical sample of the titled compound, which was 98% pure by HPLC.

PMR (CD$_3$OD): PMR according to theory.
Elemental Analysis: C$_{23}$H$_{17}$N$_3$O$_3$.0.7C$_2$H$_4$O$_2$: Calc'd For: N, 10.02; C, 69.30; H, 4.66. Found: N, 10.10; C, 69.13; H, 4.98.

EXAMPLE 17

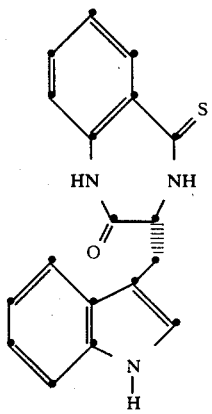

Synthesis of 3β-[(1H-indol-3-yl)methyl]-3,4-dihydro-1H-1,4-benzodiazepin-2-one-5-thione 3(S)-[(1H-Indol-3-yl)methyl]-3,4-dihydro-1H-1,4-benzodiazepin-2,5-dione (1.47 g, 4.81 mmole) was dissolved in 50 ml of dry tetrahydrofuran and treated with 1.21 g (3.00 mmole) of 2,4-bis-(4-methoxyphenyl)-2,4-dithioxo-1,3,2,4-dithiaphosphetane. The resulting mixture was stirred at room temperature overnight and concentrated, with the residue being partitioned between ethyl acetate (150 ml) and water (50 ml). The organic phase was washed with 10% sodium hydroxide solution (3×50 ml) and brine, then dried and concentrated. The crude semi-solid was flash chromatographed on silica gel (ethyl acetate-hexane, 2:1 v/v) to afford 600 mg of the title compound along with 750 mg of regioisomeric products and starting material.

The analytical sample had m.p. 166.5°–167.5° C.
IR (KBr, partial): 3400, 1680, 1580, 1200, 740 cm$^{-1}$.
PMR (CD$_3$OD): according to theory.
Elemental Analysis: C$_{18}$H$_{15}$N$_3$OS.1/4H$_2$O: Calc'd: N, 12.89; C, 66.33; H, 4.79. Found: N, 12.58; C, 66.50; H, 4.84.

EXAMPLE 18

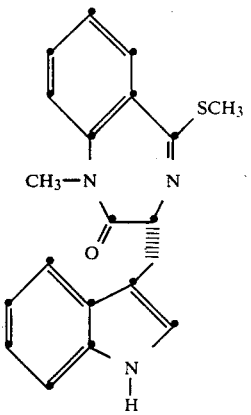

Synthesis of 1-methyl-3β-[(1H-indol-3-yl)methyl]-5-methylthio-1H-1,4-bendiodiazepin-2-one To a rapidly-stirring solution of 30 ml of toluene and 15 ml of 40% sodium hydroxide solution was added 3(S)-[(1H-indol-3-yl)methyl]-3,4-dihydro-1H-1,4-benzodiazepin-2-one-5-thione (450 mg, 1.4 mmole) and tetra-n-butyl-ammonium hydrogen sulfate (203 mg, 0.6 mmole). The mixture was stirred for an additional 15 minutes at room temperature, then iodo methane (0.175 ml, 2.8 mmole) was added and stirring was continued for still an additional 15 minutes. The phases were separated and the aqueous layer was extracted with ethyl acetate (2×30 ml). The combined organic extracts were washed with water and brine, then dried (MgSo$_4$) and concentrated to give a yellow oil. Silica gel chromatography (hexane-ethyl acetate, 2:1 v/v) afforded the desired product in pure form, R$_f$=0.4. Recrystallization from ethyl acetate-ether gave the analytical product, m.p. 90°–91° C.

MS (20 ev): 349 (M+), 220, 130 (base peak).
PMR (CDCl$_3$): according to theory.

Elemental Analysis: C₂₀H₁₉N₃OS: Calc'd: N, 12.02; C, 68.74; H, 5.48. Found: N, 12.10; C, 68.58; H, 5.71.

EXAMPLE 19

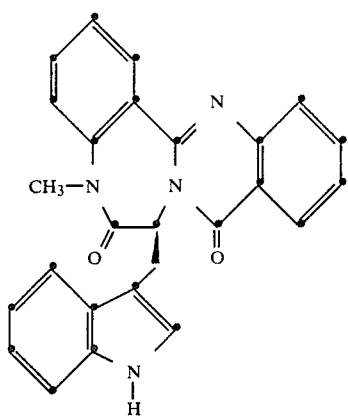

after 2 hours. After 3 hours reaction time, excess anthranilic acid was removed under reduced pressure (sublimation) and the residual brown solid chromatographed on silica gel (chloroform-methanol 95:5 v/v). The title compound I was isolated in 60% yield as a beige solid. MS (20 ev): 420 (M+), 362, 251, 234, 170, 130.

PMR(CD₃OD): 2.82 (1H, dxd, J-15.9), 2.94 (1H, dxd, J=15.9), 3.41 (3H, s, CH₃), 6.81 (1H, t, J=9, 7β-proton), 6.83 (1H, s, indole C-2), 6.97 (1H, t, J=8), 7.05 (1H, t, J=8), 7.25 (1H, d, J=8), 7.36 (1H, d, J=8), 7.53 (1H, t, J=7), 7.57 (1H, d, J=9), 7.62 (1H, d, J=9), 7.76 (1H, d, J=8), 7.83 (1H, d, J=8), 7.85 (1H, t, J=7), 8.15 (1H, d, J=8), 8.16 (1H, t, J=8).

Elemental Analysis: C₂₆H₂₀N₄O₂.0.4H₂O: Calc'd For: N, 13.10; C, 73.02; H, 4.90. Found: N, 12.97; C, 73.15; H, 4.89.

EXAMPLE 20

Representative formula I compounds listed were tested as CCK-antagonists (in I-CCK-8 pancreas and ¹²⁵I-CCK Brain assays) with results, as tabulated in the following table.

TABLE 1

| Compound from Example | Formula I Substituents | | | | Configuration At Position 7 | I-CCK-8 Pancreas IC₅₀ (EM) | ¹²⁵I-CCK Brain IC₅₀ (EM) |
|---|---|---|---|---|---|---|---|
| | X¹ | X² | R | R¹ | | | |
| * | H | H | CH₂-(indol-3-yl) | H | S | 76 | 110 |
| 13 | H | H | -CH₂-(indol-3-yl) | H | R | 67 | 100 |
| 16 | H | H | -CH₂-(4-hydroxyphenyl) | H | S | 100 | 100 |
| 15 | H | H | H | H | — | 100 | 100 |
| 14 | H | H | CH₃ | H | S | 100 | 100 |
| 19 | H | H | -CH₂-(indol-3-yl) | CH₃ | S | 104 | 51 |

*Known compound of formula Ia (discussed in Background, above) for comparison

Synthesis of
5-methyl-7β-[(1H-indol-3-yl)methyl]quinazolino(3,2-D)(1,4)benzodiazepin-6,9(5H,7H)-dione hydrate 1-Methyl-3(S)-[(1H-indol-3-yl)methyl]-5-methylthio-1H-1,4-benzodiazepin-2-one (34.3 mg, 0.1 mmole) and anthranilic acid (13.7 mg, 0.1 mmole) were mixed and heated at 175° C. After 1 hour, 13.7 mg more of anthranilic acid was added to the melt, and another equivalent The data shows that the potency of the compound of Example 13 is improved compared with the formula Ia compound. More dramatically, the compound of Example 19 has a substantial change in selectivity compared with the other compounds and especially the formula Ia and Example 13 compounds.

What is claimed is:
1. A compund of the formula:

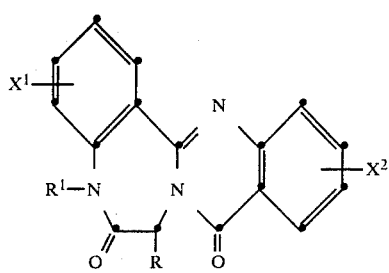

(I)

wherein:

X¹ and X² are independently selected from H, Br, Cl, F, OH,

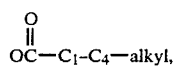

and O-C₁-C₄-alkyl;

R is H; C₁-C₅-alkyl; hydroxy-C₁-C₄alkyl; C₃-C₇-cycloalkyl; C₁-C₅-aralkyl, wherein the aryl moiety is phenyl or naphthyl, which is unsubstituted or monosubstituted on the aromatic ring by Br, Cl, F, OH, O-C₁-C₄-alkyl, O-CH₂-phenyl,

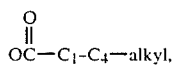

NO₂, CN, CF₃, or OSO₃H; CH₂-imidazole; CH₂-thiophene; CH₂-2-indole; CH₂-3-indole; CH₂-2-indoline; CH₂-3-indoline;

CH₂CH₂SCH₃; or

where R² is C₁-C₄-alkyl; C₃-C₇-cycloalkyl; C₁-C₄-aralkyl, wherein the aryl moiety is phenyl or naphthyl, which is unsubstituted or monosubstituted on the ariomatic ring by Br, Cl, F, OH, O-C₁-C₄-alkyl,

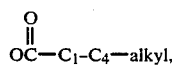

C₁-C₄-alkyl, CF₂, NO₂, NH₂, N(CH₃)₂, CN or S-C₁-C₄-alkyl; 2-indole or 3-indole, which is unsubstituted or monosubstituted by F, Cl, Br, OH, NO₂ or O-C₁-C₄-alkyl; thiophene; imidazole; benzofuran; benzothiophene; or benzimidazole; and R¹ is H, or C₁-C₄-alkyl, or (CH₂)ₙCO₂H, where n is 1 to 3;

(excluding compounds where X¹ and X² are H, R is

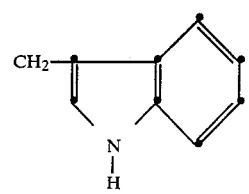

and R¹ is H) and pharmaceutically-acceptable salts thereof.

2. Compounds according to claim 1, wherein R¹ is H, CH₃ or (CH₂)CO₂H and R is H, C₁-C₅-alkyl, or C₁-C₄-aralkyl.

3. Compounds according to claim 1 wherein R is CH₃, p-hydroxyphenylmethyl or, if R¹ is not H, indolylmethyl.

4. Compounds of claim 3, wherein X¹ and X² are H and R¹ is CH₃.

5. Compounds of claim 1, wherein R is 1H-indol-3-ylmethyl and R¹ is CH₃.

6. A pharmaceutical composition for inhibiting cholecystokinin containing a cholecystokinin-inhibiting amount of a compound of claim 1 and pharmaceutically acceptable carrier.

7. A method of effecting cholesystokinin inhibition in mammals which comprises administering an effective amount of a compound according to claim 1.

8. A process for preparing compounds of formula I:

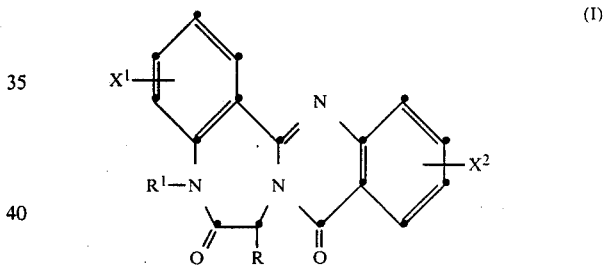

(I)

wherein:

X¹ and X² are independently selected from H, Br, Cl, F, OH, O-C₁-C₄-alkyl, and

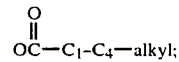

R is H; C₁-C₅-alkyl; hydroxy-C₁-C₄alkyl; C₃-C₇-cycloalkyl; C₁-C₅-aralkyl, wherein the aryl moiety is phenyl or naphthyl, which is unsubstituted or monosubstituted on the aromatic ring by Br, Cl, F, OH, O-C₁-C₄-alkyl, O-CH₂-phenyl,

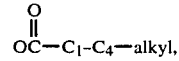

NO₂, CN, CF₃, and OSO₃H; CH₂-imidazole; CH₂-thiophene; CH₂-2-indole; CH₂-3-indole; CH₂-2-indoline; CH₂-3-indoline;

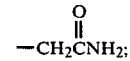

-continued

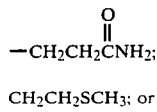

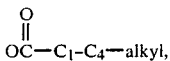

where $R^2$ is $C_1$-$C_4$-alkyl; $C_3$-$C_7$-cycloalkyl; $C_1$-$C_4$-aralkyl, wherein the aryl moiety is phenyl or naphthyl, which is unsubstituted or monosubstituted on the aromatic ring by Br, Cl, F, OH, O-$C_1$-$C_4$-alkyl,

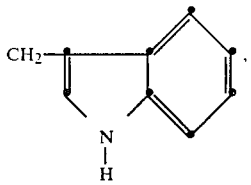

$C_1$-$C_4$-alkyl, $CF_2$, $NO_2$, $NH_2$, $N(CH_3)_2$, CN or S-$C_1$-$C_4$-alkyl; 2-indole or 3-indole, which is unsubstituted or monosubstituted by F, Cl, Br, OH, $NO_2$ or O-$C_1$-$C_4$-alkyl; thiophene; imidazole; benzofuran; benzothiophene; or benzimidazole; and $R^1$ is H, or $C_1$-$C_4$-alkyl or $(CH_2)_nCO_2H$, where n is 1 to 3;

(excluding compounds where $X^1$ and $X^2$ are H, R is

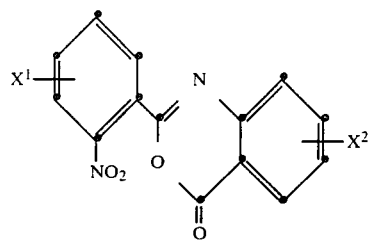

and $R^1$ is H) and pharmaceutically-acceptable salts thereof, which comprises:

(a) reducing a compound of formula V:

(V)

to obtain the amine of formula VI:

(VI)

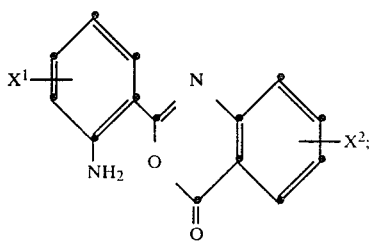

(b)
(i) reacting a compound of formula VI with $$R^3HN-\overset{R}{\underset{|}{CH}}-\overset{O}{\underset{\|}{C}}-OH$$

wherein $R^3$ is a removable amino blocking group, followed by deblocking, or (ii) reacting a compound of formula VI with an amino acid chloride hydrochloride in an aprotic solvent to obtain a compound of formula VIIIa:

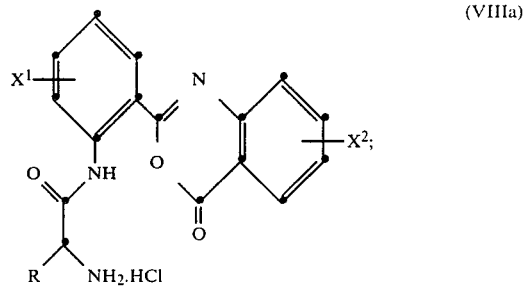

(VIIIa)

(c) heating a compound of formula VIIIa to obtain a compound of formula I where $R^1$ is H, and alkylating a compound of formula I where $R^1$ is H to obtain a compound of formula I where $R^1$ is $C_1$-$C_4$-alkyl or $(CH_2)_nCO_2H$, where n is 1 to 3; or which comprises (d) reacting a compound of formula V with an amino acid ester of the formula

wherein $R^4$ is $C_1$-$C_4$-alkyl, phenyl or phenyl-$C_1$-$C_4$-alkyl in an aprotic reaction medium to obtain a compound of formula IVa:

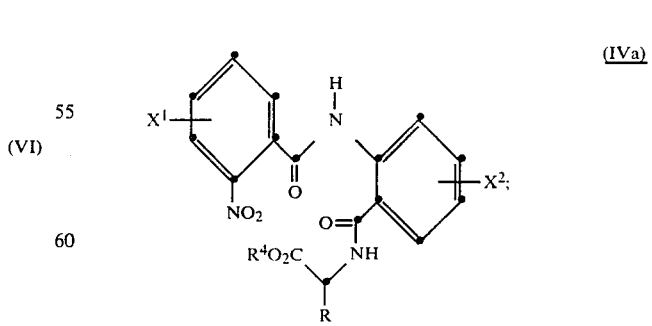

(IVa)

(e) reducing a compound of formula IVa with hydrogen in the presence of a Group VIII metal catalyst to obtain the compound having formula III:

(III) 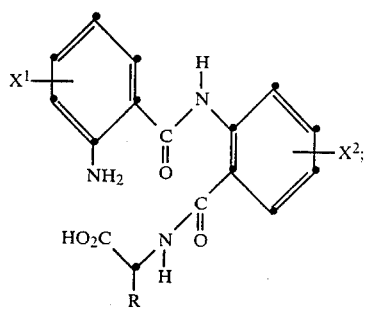

(f) cyclodehydrating the compound of formula III to obtain a compound having formula I where $R^1$ is H, then alkylating the compound of formula I where $R^1$ is H to obtain a compound having formula I where $R^1$ is $C_1$–$C_4$-alkyl or $(CH_2)_nCO_2H$, where n is 1 to 3.

9. The process of claim 8, steps a through c, wherein R is H and $R^3$ is tert-butyloxycarbonyl.

10. The process of claim 8, steps d through f, wherein R is H, aryl-$C_1$–$C_4$alkyl, or $C_1$–$C_5$-straight or branched-chain alkyl.

11. The process of claim 8, steps d through f, wherein R is H, p-hydroxyphenylmethyl or $CH_3$.

* * * * *